United States Patent
Iwase

(10) Patent No.: US 9,265,418 B2
(45) Date of Patent: Feb. 23, 2016

(54) IMAGE PROCESSING APPARATUS, IMAGE PROCESSING METHOD, AND PROGRAM

(71) Applicant: CANON KABUSHIKI KAISHA, Tokyo (JP)

(72) Inventor: Yoshihiko Iwase, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 13/747,755

(22) Filed: Jan. 23, 2013

(65) Prior Publication Data
US 2013/0194546 A1 Aug. 1, 2013

(30) Foreign Application Priority Data
Jan. 27, 2012 (JP) ................... 2012-015248

(51) Int. Cl.
| | | |
|---|---|---|
| *A61B 3/14* | (2006.01) | |
| *A61B 3/00* | (2006.01) | |
| *A61B 3/10* | (2006.01) | |
| *G06T 7/00* | (2006.01) | |

(52) U.S. Cl.
CPC ............... *A61B 3/14* (2013.01); *G06T 7/0012* (2013.01); *G06T 2207/10101* (2013.01); *G06T 2207/30041* (2013.01)

(58) Field of Classification Search
CPC ........ A61B 3/14; A61B 3/103; A61B 3/1225; A61B 3/113; A61B 3/1015
USPC .................. 351/206, 205, 221, 210, 200, 246
See application file for complete search history.

(56) References Cited

U.S. PATENT DOCUMENTS

| | | | |
|---|---|---|---|
| 8,137,271 B2 | 3/2012 | Bille | |
| 2008/0100612 A1* | 5/2008 | Dastmalchi et al. | 345/418 |
| 2010/0060853 A1* | 3/2010 | Bille | 351/206 |
| 2010/0160789 A1* | 6/2010 | Dilworth et al. | 600/476 |
| 2010/0228114 A1 | 9/2010 | Bille | |
| 2012/0140178 A1 | 6/2012 | Bille | |
| 2012/0143035 A1 | 6/2012 | Bille | |

(Continued)

FOREIGN PATENT DOCUMENTS

| | | |
|---|---|---|
| CN | 101778593 A | 7/2010 |
| EP | 2482249 A | 8/2012 |

(Continued)

OTHER PUBLICATIONS

Great Britain Search Report issued on Jul. 19, 2013 in corresponding application No. 1301356.0.

(Continued)

*Primary Examiner* — Dawayne A Pinkney
(74) *Attorney, Agent, or Firm* — Carter, DeLuca, Farrell & Schmidt, LLP

(57) ABSTRACT

Although a lamina cribrosa is deformed in glaucoma, in a method in a related art, a thickness of retinal layer or choroid is measured and a deformation of the lamina cribrosa is not detected. When glaucoma is diagnosed, it is desirable to analyze a shape of the lamina cribrosa and present its analysis result at a high visibility. An image processing apparatus is provided that comprises: an image obtaining unit that obtains a tomographic image of a subject's eye; an extracting unit that extracts a lamina cribrosa from the tomographic image; and a display control unit that controls a display means to display a display form showing a shape of the extracted lamina cribrosa.

32 Claims, 10 Drawing Sheets

(56) References Cited

U.S. PATENT DOCUMENTS

2012/0194782 A1* 8/2012 Imamura ............... 351/206
2013/0093870 A1* 4/2013 Shibutani ............... 348/78

FOREIGN PATENT DOCUMENTS

| JP | 2002-513310 A | 5/2002 |
| JP | 2008-073099 A | 4/2008 |
| JP | 2008-209166 A | 9/2008 |
| JP | 2008-272256 A | 11/2008 |
| JP | 2010-201174 A | 9/2010 |
| JP | 2011-072716 A | 4/2011 |
| JP | 2012-100811 A | 5/2012 |
| WO | 2006/022045 A | 3/2006 |
| WO | 2008058386 A1 | 5/2008 |
| WO | 2012/063390 A | 5/2012 |

OTHER PUBLICATIONS

Lee et al., "Visualization of the Lamina Cribrosa Using Enhanced Depth Imaging Spectral-Domain Optical Coherence Tomography", American Journal of Ophthalmology, Jul. 2011, vol. 152, No. 1, pp. 87-96.

Chinese Office Action issued in corresponding application No. 201310031091.0 on Aug. 27, 2014.

* cited by examiner

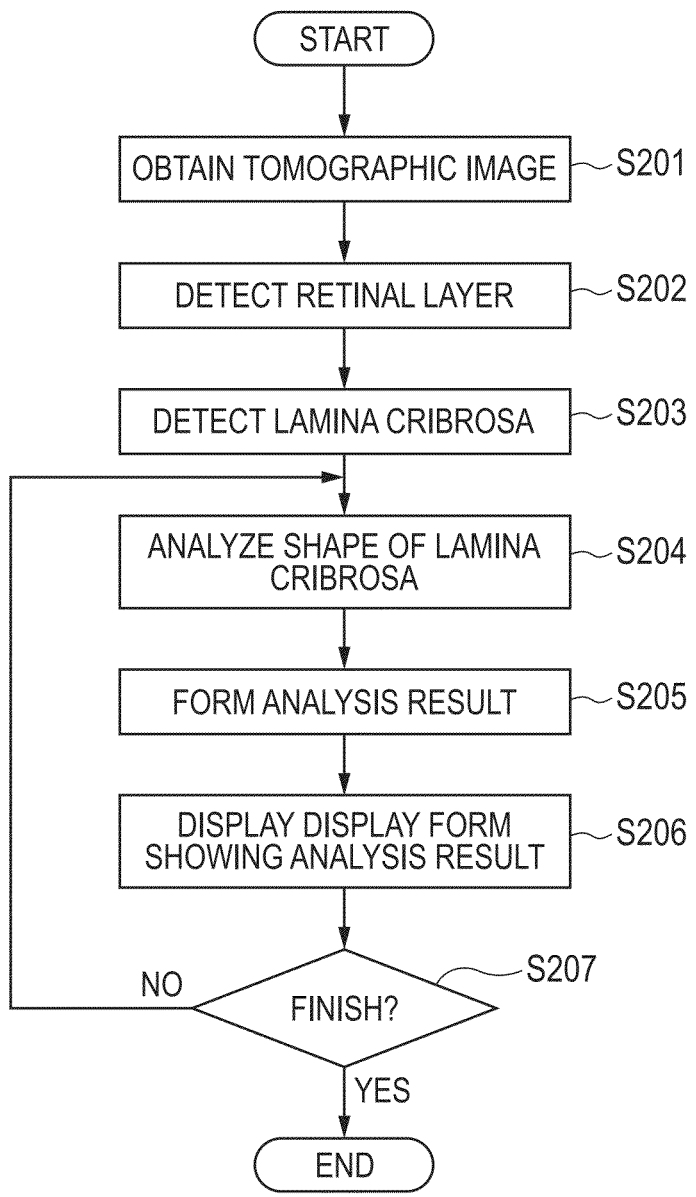

IMAGE PROCESSING APPARATUS, IMAGE PROCESSING METHOD, AND PROGRAM

BACKGROUND OF THE INVENTION

1. Field of the Invention

The present invention relates to an image processing apparatus, an image processing method, and a program for, in particular, processing a tomographic image of a subject's eye (i.e. an eye to be examined).

2. Description of the Related Art

A tomographic imaging apparatus such as an OCT (Optical Coherence Tomography) apparatus can three-dimensionally observe a state in a retinal layer of an eye. In recent years, the tomographic imaging apparatus has been highlighted because it is useful to perform more accurately a diagnosis of a disease. As a form of the OCT, there is a TD-OCT (Time Domain OCT) in which a light source with a wide bandwidth and a Michelson interferometer are used. The TD-OCT is constructed in such a manner that by scanning a delay of a reference arm, interference light with backward scattered light of a signal arm is measured and information of depth decomposition is obtained. However, it is difficult to obtain a high-speed image using TD-OCT because a plurality of A-scans have to be combined to give a B-scan, a plurality of which have to be combined to give the 3-D tomographic image, and this consecutive scanning process takes time. Therefore, as a method of obtaining an image at a higher speed, an SD-OCT (Spectral Domain OCT) has been known as an OCT for obtaining an interferogram by a spectroscope by using a light source with a wide bandwidth. In this method, Fourier transforms are used to interpret images that can be taken all at once rather than as individual scans, thus saving time over the TD-OCT. An SS-OCT (Swept Source OCT) is a method of measuring a spectral interference using a photodetector of a single light channel and using a high-speed wavelength sweep light source as a light source.

In this instance, if a form change of a retina in a tomographic image can be measured, a degree of progress of a disease such as glaucoma or the like and a degree of recovery after a treatment can be quantitatively diagnosed. In order to quantitatively measure such form changes of the retina, such a technique that boundaries among layers of the retina are detected from a tomographic image by using a computer and a thickness of layer is measured has been disclosed in Japanese Patent Application Laid-Open No. 2008-073099A. A technique for measuring a thickness of choroid (coat membrane) has also been disclosed in Japanese Patent Application Laid-Open No. 2011-072716 for the purpose of diagnosing early glaucoma.

SUMMARY OF THE INVENTION

In the case of glaucoma, a fact that an area called "lamina cribrosa" is deformed has been known. It is presumed that since an optic nerve fiber in the lamina cribrosa is pressed, a transport of a nerve nutritional factor by a retrograde axonal transport is obstructed and a nerve ganglion cell dies. The method in the related art intends to measure a thickness of retinal layer or choroid and does not detect a deformation of the lamina cribrosa. To diagnose glaucoma, it is effective that the lamina cribrosa is measured and a measurement result is used in the diagnosis.

The invention is made in consideration of the foregoing problems and it is an object of the invention to present an analysis result of a shape of lamina cribrosa at a high visibility.

In order to solve the foregoing problems, the present invention provides an image processing apparatus comprises: an image obtaining unit for obtaining a tomographic image of an eye to be examined; a detection unit for detecting a lamina cribrosa from the tomographic image of the eye; and a display control unit for controlling a display means to display a display form showing a shape of the detected lamina cribrosa.

According to the invention, the analysis result of the shape of lamina cribrosa can be presented at a high visibility.

Further features of the present invention will become apparent from the following description of exemplary embodiments with reference to the attached drawings.

BRIEF DESCRIPTION OF THE DRAWINGS

FIG. 2 is a flowchart showing a flow for processes in an image processing apparatus.

DESCRIPTION OF THE EMBODIMENTS

Embodiments of the invention will be described hereinbelow with reference to the drawings. An image processing system having an image processing apparatus according to the embodiment is characterized in that a shape of a lamina cribrosa is analyzed and converted into a numerical value and its analysis result is displayed.

Embodiment 1

Result Obtained by Analyzing Shape of Lamina Cribrosa is Displayed by Map

Figure 1:
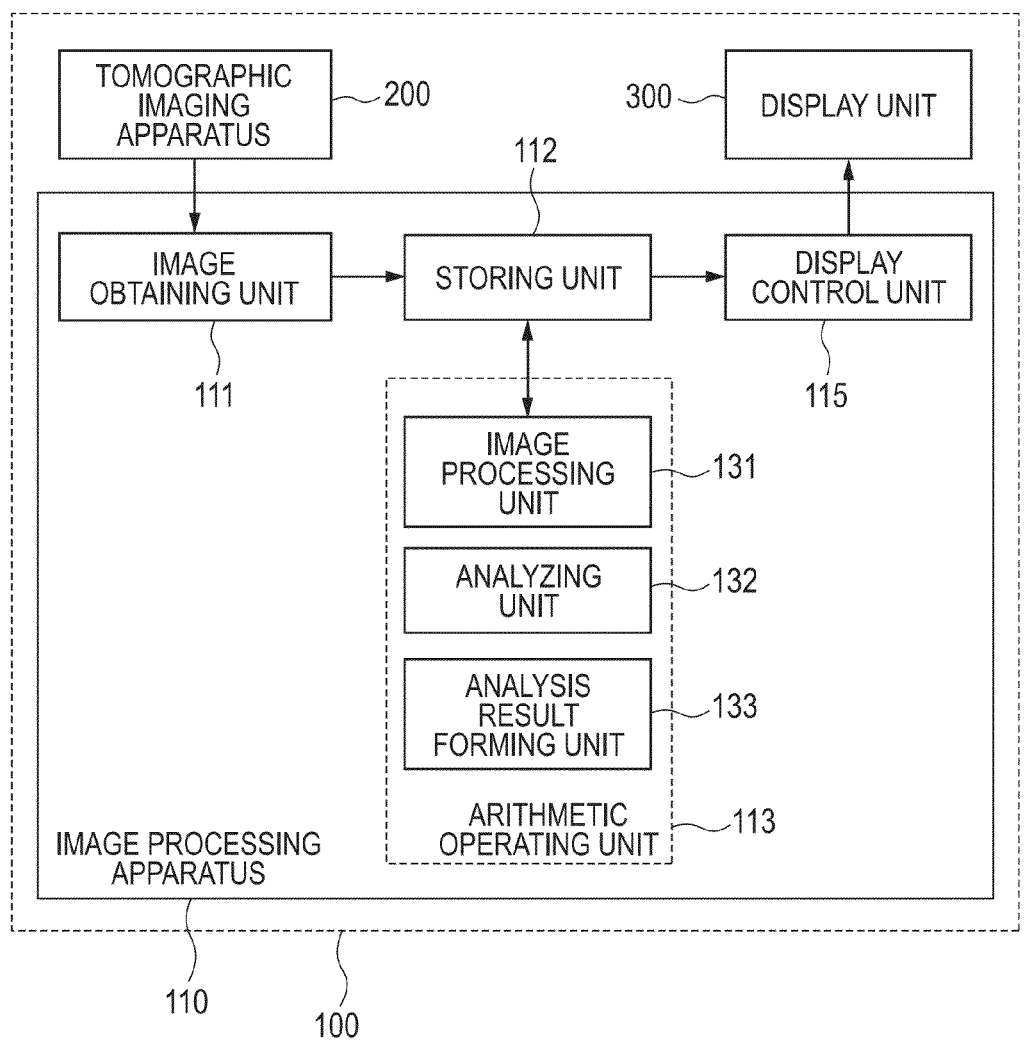
FIG. 1 is a diagram illustrating a construction of an image processing system.

FIG. 1 is a diagram illustrating a construction of an image processing system 100 having an image processing apparatus 110 according to the embodiment 1. As illustrated in FIG. 1, the image processing system 100 is constructed by connecting the image processing apparatus 110 to a tomographic imaging apparatus 200 and a display unit 300 through an interface.

The tomographic imaging apparatus 200 is an apparatus for photographing a tomographic image of an eye portion (a subject's eye, that is, an eye to be examined). An apparatus which is used for the tomographic imaging apparatus is constructed by, for example, the SD-OCT or SS-OCT. Since the tomographic imaging apparatus 200 is a well-known apparatus, its detailed description is omitted here. However, as a light source, it is desirable to use a light source for emitting light of a wavelength near 1000 nm. When the wavelength of the light source is long, it is more difficult to be influenced by scattering of a tissue as compared with that in the case of a light source using a wavelength nearer to 800 nm. Therefore, a longer wavelength of light is more suitable to photograph an image of a tissue of a deep portion (in a z direction in FIG. 8) rather than a retinal layer. As a photographing method, it is desirable to use a photographing method by an Enhanced Depth Imaging method (hereinbelow, also referred to as an EDI method). It is a method which is mainly used when the user wants to see a choroid in detail to determine a relationship between the choroid and a disease. The EDI method is a method of obtaining a tomographic image by a reverse image in a state where a position of a coherence gate is located on the rear side of the choroid. The "coherence gate" denotes a position where an optical distance of measurement light in the OCT and an optical distance of reference light are equal. This photographing method is also suitable to photograph the image of the tissue of the deep portion more than the retinal layer. As mentioned above, it is sufficient that the tomographic imaging apparatus 200 in the embodiment is an apparatus which can photograph using the OCT or photographing method suitable to photograph deep tissue.

The image processing apparatus 110 has an image obtaining unit 111, a storing unit 112, an arithmetic operating unit 113, and a display control unit 115. The arithmetic operating unit 113 comprises an image processing unit 131, an analyzing unit 132, and an analysis result forming unit 133. The image obtaining unit 111 obtains the tomographic image photographed by the tomographic imaging apparatus 200 and stores into the storing unit 112. The image processing unit 131 detects a layer (in the eye) from the tomographic image stored in the storing unit 112. The analyzing unit 132 analyzes an area serving as an analysis target. The analysis result forming unit 133 forms various kinds of data for presenting an analysis result.

A processing procedure of the image processing apparatus 110 will be described with reference to FIG. 2.

<Step S201: Obtainment of Tomographic Image>

In step S201, the image obtaining unit 111 obtains a tomographic image from the tomographic imaging apparatus 200. The tomographic image is obtained as a set of (in the embodiment, six) tomographic images photographed by radial scans, which will be described hereinafter with reference to FIGS. 4A and 4B. The obtained tomographic images are stored into the storing unit 112.

<Step S202: Detection of Retinal Layer>

Figure 8:
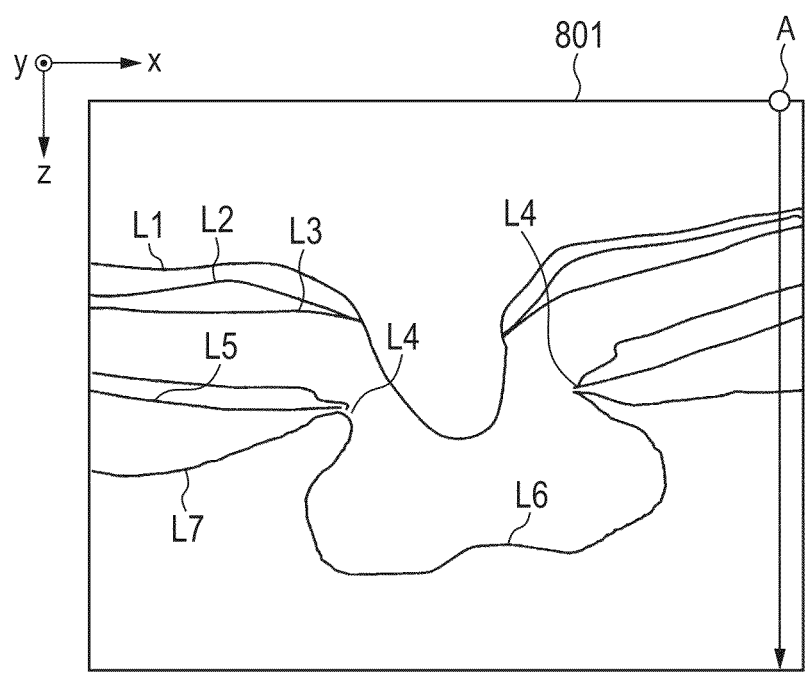
FIG. 8 is a schematic diagram of a tomographic image of an optic nerve nipple portion of a retina.

In step S202, the image processing unit 131, serving as an example of a retinal layer detecting unit, detects each area of an optic nerve nipple portion of the tomographic image obtained in step S201. The detection of each area of the optic nerve nipple portion will be described with reference to FIG. 8. FIG. 8 is a schematic diagram of a tomographic image 801 of the optic nerve nipple portion. The tomographic image is constructed by a plurality of "A-scans" (pixel train A of one line which is parallel with a z-axis direction) located on a same plane to give rise to a "B-scan" in said plane (here, in the x-z plane). In 3-dimensional data constructed by a plurality of tomographic images, an x-y plane (perpendicular to the B-scans and the direction in which a plurality of B-scans are photographed and built up) is called "C-scan". L1 denotes an inner boundary membrane (ILM or internal limiting membrane); L2, a nerve fiber layer (NFL); L3, a nerve ganglion cell layer (GCL); L4, a Bruch membrane opening (BMO); L5, a retinal pigment epithelium (RPE); L6, a lamina cribrosa (LC); and L7, a choroid (coat membrane). The image processing unit 131 detects boundaries between the areas L1 to L7.

The detection of the boundaries among the areas of the retinal layer will now be described. First, images are formed by applying a median filter and a Sobel filter to the tomographic image (hereinbelow, referred to as a "median image" and a "Sobel image" respectively). Profiles are formed from the formed median image and Sobel image for every "A-scan". In the median image, the profile of a luminance value is formed. In the Sobel image, the profile of a gradient value is formed. A peak in the profile formed from the Sobel image is detected. The boundaries between the areas of the retinal layer are detected by referring to the profile of the median image corresponding to portions before and after the detected peak or between the detected peaks.

<Step S203: Detection of Lamina Cribrosa>

In step S203, the image processing unit 131, serving as an example of a lamina cribrosa detecting unit (also regarded as an extracting unit when an image or shape or position of the lamina cribrosa is extracted from the tomographic image), detects a lamina cribrosa area from the tomographic image obtained by the image obtaining unit 111. In this case, first, the BMO (L4) as an example of a feature portion regarding the lamina cribrosa in the tomographic image in FIG. 8 is detected. In the detection of the BMO (L4), for example, an optic nerve nipple is specified by using the results of the ILM (L1) and RPE (L5) detected in step S202. In this case, particularly, it is desirable to specify an inverted depression portion of the optic nerve nipple. In the embodiment, a portion near the center of the inverted depression portion of the optic nerve nipple is specified. As a feature of the inverted depression portion of the optic nerve nipple, such conditions that the RPE (L5) does not exist and the shape of the ILM (L1) has a large gradient in the deep portion direction (the z direction in FIG. 8) can be mentioned. Indeed, these characteristics (no RPE, large gradient in the ILM, and so on) indicate a likely position of the lamina cribrosa. Therefore, a local area including each A-scan and its peripheral A-scan is set. The detection of the existence of the RPE (L5) in the local area and the gradient in the deep portion direction of the ILM (L1) are calculated, and a point near the center of the inverted depression portion of the optic nerve nipple is specified. Subsequently, by connecting a point of the RPE (L5) near the center of the inverted depression portion of the optic nerve nipple in each tomographic image with respect to all of the tomographic images, an RPE area seen as an elliptic shape in the case where it is seen in the C-scan direction is set. By setting the RPE area as an initial position and applying a proper dynamic contour model (for example, Snakes or LevelSet), the BMO (L4) is recognisable in each tomographic image. Subsequently, an edge component is traced from the edge portion specified above, that is, from the BMO edge toward the center of the inverted depression portion of the optic nerve nipple, thereby specifying the accurate position of the BMO edge. In the embodiment, first, coordinate values and edge component are examined with respect to each BMO edge. Subsequently, the position of each BMO edge is set as a start point and the edge is traced toward the center of the inverted depression portion of the optic nerve nipple. Upon tracing, the edge component at the position of each BMO edge is referred to, a search point is updated to the position where the edge component existing near the inside is closest, and the edge component which is referred to is also updated. By repeating such processes, the accurate BMO edge is specified. It is also possible to construct in such a manner that the BMO edge of the tomographic image is colored so as to be emphasis-displayed (or highlighted), a line connecting two BMO edge is overlaid to the tomographic image and is displayed, or an area surrounded by such a line and a contour of the lamina cribrosa is colored so as to be emphasis-displayed. By displaying those display states as a detection result of the lamina cribrosa, the user is enabled to observe them easily.

Subsequently, in one tomographic image (B-scan), at positions where the BMO (L4) of two points were detected, a lamina cribrosa boundary at which the BMO is set to a fixed edge is used as an initial value, the dynamic contour model such as Snakes or LevelSet mentioned above is executed, and a lamina cribrosa area (L6 in FIG. 8) is detected. In the dynamic contour model, by further using a probability atlas, the area detection may be performed by using a spatial existence probability of the lamina cribrosa.

Although the example in the case where the detection unit detects the lamina cribrosa area from the tomographic image which was automatically obtained has been described here, the operator may correct the automatic detection result by using an operating unit (not shown) or may manually set the lamina cribrosa area. After the operator has manually selected a part of the obtained tomographic image as a range where the lamina cribrosa is to be detected, the detection unit may automatically detect the lamina cribrosa from the selected range. For example, the user may set a cursor onto the tomographic image displayed on a display such as display unit 300 and clicks at a plurality of positions outlining or otherwise defining the shape and position of the lamina cribrosa, and the lamina cribrosa area may be detected on the basis of those positions. Before step S203, a discriminating unit (not shown) may automatically discriminate whether or not the lamina cribrosa area or the optic nerve nipple can be detected from the tomographic image. The discriminating unit may automatically discriminate whether or not the tomographic image is photographed as an image including the optic nerve nipple. If no optic nerve nipple is included in the tomographic image, the processing routine does not advance to step S203 but it is desirable that the display control unit 115 allows an error message to be displayed to the display as a display form showing that the analysis regarding the lamina cribrosa cannot be performed in the obtained tomographic image. Even when the optic nerve nipple is included in the tomographic image, in the case of a tomographic image which is not photographed by the EDI method or SS-OCT, there is a case where resolution is not sufficient for the lamina cribrosa to be automatically analyzed or the photographing range in the depth direction is not sufficient for the lamina cribrosa to be photographed. Also in this case, it is desirable that the display control unit 115 allows the error message to be displayed on the display.

<Step S204: Analysis of Shape of Lamina Cribrosa>

In step S204, the analyzing unit 132 performs various kinds of analysis on the basis of a result of the area detected in the optic nerve nipple portion. As a case of analyzing the lamina cribrosa area, a case of analyzing a curvature of the shape, a case of performing the analysis by Bowing Angle, and a case of analyzing a size ratio between the lamina cribrosa area and the MBO will be described.

<Calculation of Curvature of Lamina Cribrosa>

Figure 3A:
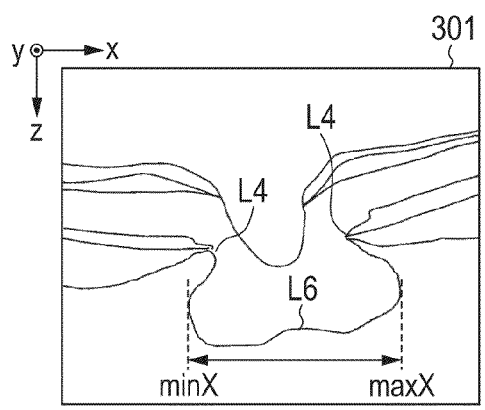
FIGS. 3A, 3B, 3C and 3D are diagrams for describing a shape analysis.

First, a case of calculating the curvature will be described by using a tomographic image 301 in FIG. 3A. In FIG. 3A, an axis of abscissa indicates an x coordinate and an axis of ordinate indicates a z axis. L4 denotes the MBO and L6 denotes the lamina cribrosa. The lamina cribrosa L6 is flanked by two points of the MBO (L4) in the 2-D tomographic image and a curvature of a boundary line between a position minX where the x coordinate is minimum and a position maxX where the x coordinate is maximum is calculated. A curvature κ can be obtained by calculating the following equation (1) at each point of the boundary line. By a sign of the curvature κ, whether the shape is upwardly convex or downwardly convex can be known and a degree of curve of the shape can be known by a magnitude of a numerical value. Therefore, now assuming that a state where the shape is upwardly convex is shown by "+" and a state where the shape is downwardly convex (or concave) is shown by "−", in the lamina cribrosa L6 of each tomographic image, if the sign of the curvature changes as follows, with a −(concave) area, a +(convex) area, and then a −(concave) area, the shape of the lamina cribrosa resembles a W shape. That is, by calculating the curvature at each point, whether the shape of lamina cribrosa is a downwardly convex shape or a W shape (or indeed another shape) can be grasped.

$$\kappa = \frac{\frac{d^2 z}{dx^2}}{\left(1 + \left(\frac{dz}{dx}\right)\right)^{\frac{3}{2}}} \quad (1)$$

<Analysis by Bowing Angle of Lamina Cribrosa>

Figure 3B:
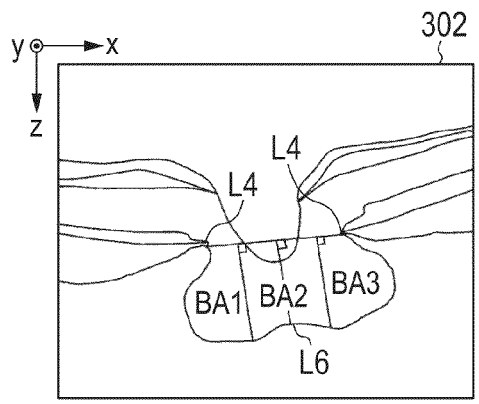

A case of analyzing by Bowing Angle as an analyzing method of the shape will be described by using a tomographic image 302 in FIG. 3B. The analyzing method of Bowing Angle will now be described. According to Bowing Angle, two points of the BMO (L4) are connected by a straight line and the straight line is itself divided into four lines. Perpendicular lines BA1, BA2, and BA3 are drawn from division points of the straight line between the two BMO points to the lamina cribrosa. The shape of the lamina cribrosa can be obtained by calculating the following equation (2) by using the lengths of those perpendicular lines. In the equation (2), a numerical value of the length (distance) of each perpendicular line is input to BA1, BA2, and BA3. In the equation (2), the larger the numerical value is (plus side), the more downwardly convex the shape, and the smaller the numerical value is (minus side), the greater the W shape. That is, Bowing Angle is an index which can grasp the shape of the lamina cribrosa from the sign and the numerical value.

$$BowingAngle = BA2 - \frac{BA1 + BA5}{2} \quad (2)$$

Bowing Angle may be calculated by a ratio instead of the numerical value. In this case, it is calculated by the following equation (3). In the equation (3), when the ratio is equal to 1 or more, the shape becomes the downwardly convex (concave) shape, and when the ratio is less than 1, the shape becomes the W shape.

$$BowingAngleRatio = BA2 \bigg/ \left(\frac{BA1 + BA5}{2}\right) \quad (3)$$

<Analysis of Size Ratio Between Lamina Cribrosa Area and BMO>

Figure 3C:
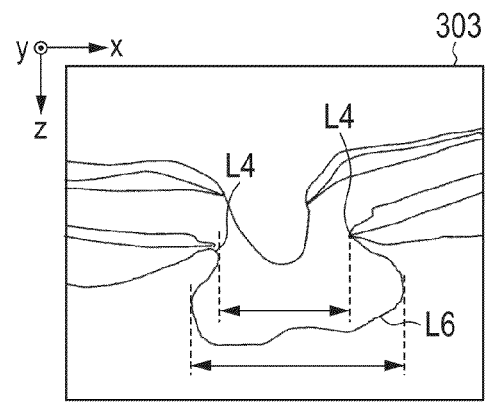
Figure 3D:
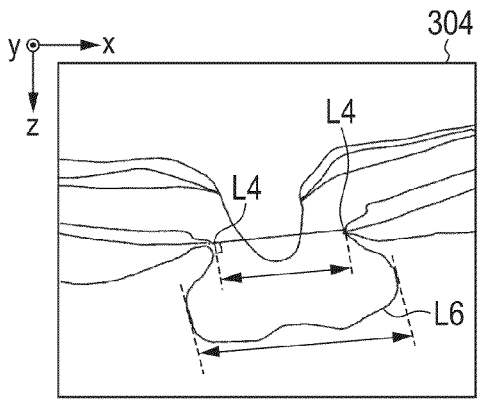

Subsequently, a case of analyzing a size ratio between the lamina cribrosa area and the BMO will be described with reference to FIGS. 3C and 3D. FIG. 3C illustrates an example in the case where in a tomographic image 303, perpendicular (here, vertical) lines are drawn from the BMO (L4) and the lamina cribrosa L6, distances between them are measured, and a ratio between the distances is analyzed. FIG. 3D illustrates an example in the case where in a tomographic image 304, a distance of the line connecting the BMO (L4) and a distance between the lamina cribrosa L6 which are in parallel with the connecting line between the two points of the BMO are measured and a ratio between those distances is analyzed. The size ratio between the lamina cribrosa area and the BMO obtained as mentioned above is analyzed by the foregoing method.

Analysis parameters which are used when the analyzing unit 132 analyzes the shape of the lamina cribrosa are not limited to those mentioned above. An area (an area surrounded by the line connecting L4 and L4 and L6 in FIG. 3D) in the lamina cribrosa area, a volume (a value obtained by calculating the area in each tomographic image and developing into a 3-dimensional shape), a thickness (a distance of a perpendicular drawn from the line connecting L4 and L4 to L6 in FIG. 3D), and the like are also used.

<Step S205: Creation of Display Form Showing Analysis Result>

Figure 4A:
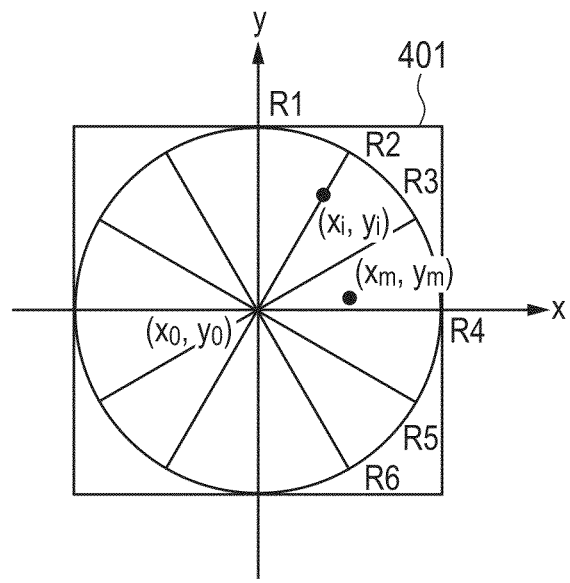
FIGS. 4A and 4B are diagrams illustrating an example of a photographing pattern and a photographing position.
Figure 4B:
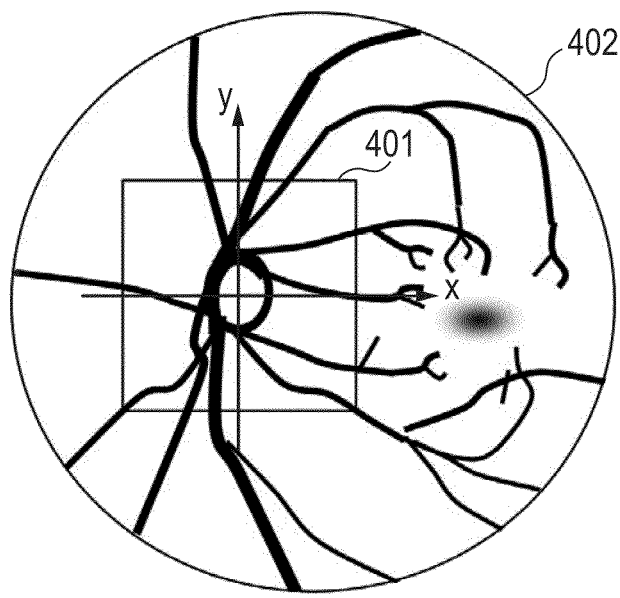

In step S205, the analysis result forming unit 133 forms a 2-dimensional map for outputting an analysis result of the analyzing unit 132 in step S204. First, a case of forming the map from the analysis result of the curvature will be described with reference to FIGS. 4A and 4B. An example in the case of forming a 2-dimensional map from a set of tomographic images photographed by the radial scans will be described here. FIG. 4A illustrates a radial scan pattern. FIG. 4B illustrates an image at a scanning position 401 on a fundus image 402. In FIG. 4A, a case of six radial scans (R1 to R6) will be described. At each point (for example, coordinates $(x_i, y_i)$ in the diagram) of the 2-dimensional map, a distance to a center $(x_0, y_0)$ of the map and an angle are calculated. By using the distance calculated at each point, a correspondence point of the x coordinate in the tomographic image can be obtained. In the radial scans, since there are no data in a region other than a range of a circle drawn by setting a center of the tomographic image to a reference, even in the 2-dimensional map, the corresponding data does not exist in a region other than the circular area. A corresponding slice number can be obtained from the angle corresponding to the center of the map calculated at each point.

By obtaining the position of the corresponding tomographic image and the corresponding slice number at each point of the 2-dimensional map, the analysis result forming unit 133 can form a map from a value of the curvature analyzed in the analyzing unit 132. In this instance, for example, if the corresponding tomographic image does not exist like $(x_m, y_m)$ in FIG. 4A, a value of the nearest tomographic image (R4 in the diagram) is substituted. In this case, as shown at 501 in FIG. 5A, a map in which a curvature value of the corresponding coordinates in the most adjacent tomographic image is input at each point of the map is formed. Therefore, a map in which a value changes at an intermediate position between the adjacent tomographic images is formed. It is now assumed that the map 501 is constructed by: a color map 511 of the curvature value or a map 511 of gray scale; and a color bar 521 or a gray scale bar 521. As for a color of the color map 511, a value of the analysis result and a value of the color bar 521 correspond.

Figure 5A:
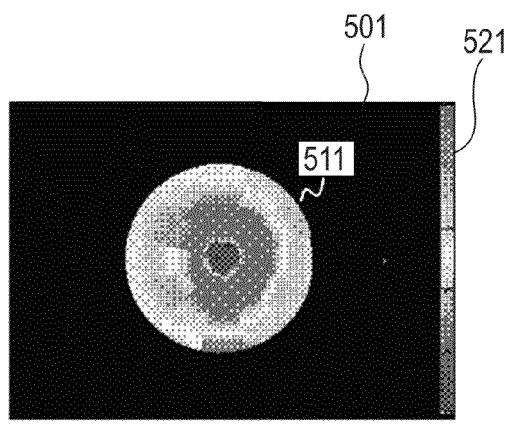
FIGS. 5A, 5B, 5C and 5D are diagrams for describing an example of presentation of an analysis result.
Figure 5B:
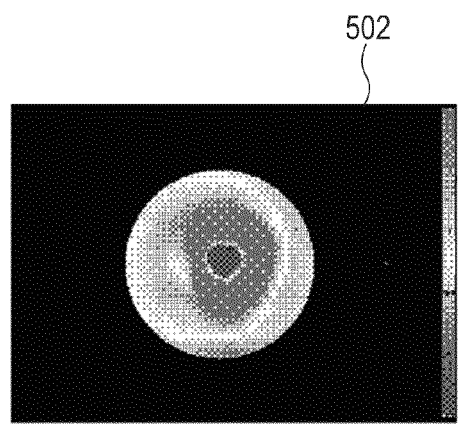
Figure 5C:
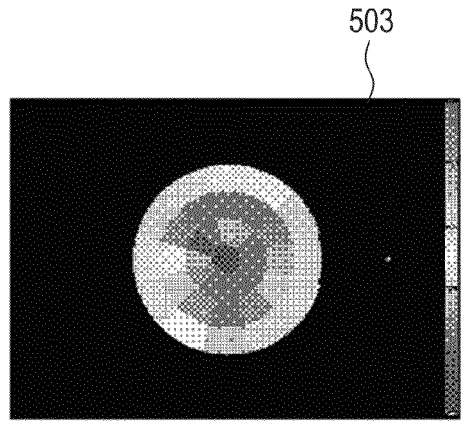

In the map 501, although an example of the map in which the curvature value of the corresponding coordinates in the most adjacent tomographic image is input has been shown, it is not limited to such a map. For example, at a coordinate point such as $(x_m, y_m)$ in FIG. 4A, a value corresponding to a ratio between the distances to both of the adjacent tomographic images (in the diagram, R3 and R4) may be substituted. That is, since the value is calculated by the ratio between the distances to the adjacent tomographic images, as shown at 502 in FIG. 5B, a map in which the value changes continuously between the tomographic images is formed. Further, in FIGS. 5A and 5B, a value is averaged every predetermined radius and obtained average values may be displayed as a map. An example in the case where the value in FIG. 5A is averaged at the predetermined radius is shown at 503 in FIG. 5C.

Figure 5D:
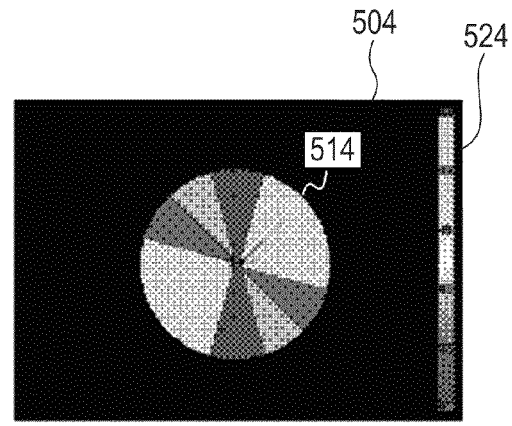

Subsequently, a case where the analysis result forming unit 133 forms a 2-dimensional map from the analysis result of Bowing Angle will be described with reference to FIG. 5D. An example in the case of forming a 2-dimensional map from a group of tomographic images photographed by the radial scans will be also described here with reference to FIG. 4A. In the case of Bowing Angle, unlike the case of the curvature mentioned above, one numerical value corresponds to one tomographic image. Therefore, if the slice number of the corresponding tomographic image is obtained at each point of the 2-dimensional map by the same method as that mentioned above, the numerical value of Bowing Angle which the tomographic image has is input to the coordinate point of the map. Thus, the map of Bowing Angle becomes a map as shown at 504 in FIG. 5D. It is now assumed that the map 504 is constructed by: a color map 514 of the Bowing Angle value or a map 514 of a gray scale; and a color bar 524 or a gray scale bar 524.

An example has been described herein for the case of forming the maps such as curvature map, Bowing Angle map, and the like from the values of various kinds of analysis results. As another example, it is also possible to construct in such a manner that if the storing unit 112 has a standard database in correspondence to various kinds of analyzing methods, the analysis result forming unit 133 forms a degree of conformance to the standard database as a map. The standard database is formed from data of a number of normal eyes and is formed by integrating data filtered by race and/or by age. In the field of the department of ophthalmology, the data may be classified on the basis of a parameter such as an eye axis length or the like that is peculiar to the eye. For example, whether or not the value of Bowing Angle lies within a range of values in the standard database is discriminated and a value which can discriminate such information is input into the map.

<Step S206: Display of Display Form Showing Analysis Result>

Figure 6A:
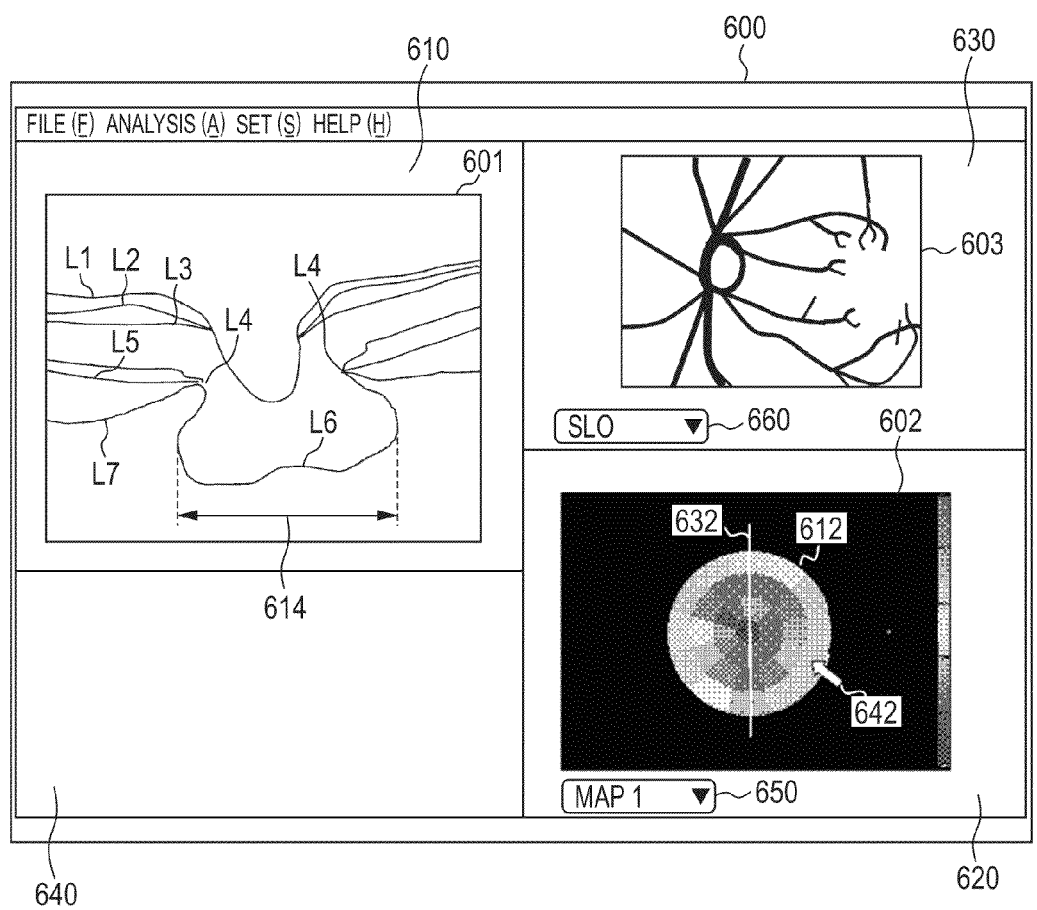
FIGS. 6A and 6B are diagrams illustrating an example of a display of an image processing apparatus.
Figure 6B:
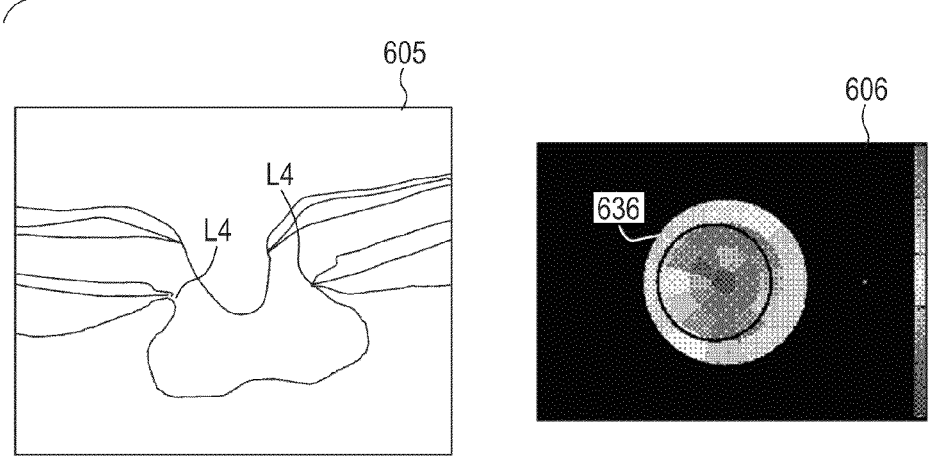

In step S206, the display control unit 115 displays the tomographic image, the detection result of the layer detected in the image processing unit 131, and the various kinds of analysis results (maps, numerical values) formed in the analysis result forming unit 133 to the display unit 300. This process will now be described with reference to FIGS. 6A and 6B. FIGS. 6A and 6B illustrate an example of a display screen which is displayed to the display unit 300 in this using form. In FIGS. 6A and 6B, there are shown: a tomographic image observing display screen 600; a tomographic image display unit 610; a fundus image display unit 630; a first analysis result display unit 620; a second analysis result display unit 640; a first display switching unit 650; and a second display switching unit 660. In the following embodiment, a description will be made on the assumption that the tomographic image is displayed to the tomographic image display unit 610 and the map is displayed to the first analysis result display unit 620.

FIG. 6A illustrates an example of a case where a tomographic image 601 and a curvature map 602 are displayed on the tomographic image observing display screen 600 side by side. They may further be displayed next to the fundus image 603. In the diagram, there are shown: the tomographic image

601; an image obtained by superimposing and displaying solid lines of colors which differ every layer onto the tomographic image as segmentation results (L1 to L7) showing detection results of the respective layers of the retinal layer; and a curvature map in which the analysis results of the shape of the lamina cribrosa are shown as a 2-dimensional map. In the curvature map 602, a display range of a color map 612 of the curvature value corresponds to an area 614 (range defined by two broken lines and a double-headed arrow) of the lamina cribrosa in the tomographic image 601.

FIG. 6B illustrates an example in which when a tomographic image 605 and a curvature map 606 are displayed on the tomographic image observing display screen 600, a line 636 is displayed connecting the positions of the BMO (L4) in each of the plurality of tomographic images (of which only one is displayed). As illustrated in FIG. 6B, by superimposing and displaying the positions of the BMO onto the lamina cribrosa area of the 2-dimensional map, a displacement state of the lamina cribrosa by a highly nearsighted (or short-sighted) eye or the like can be easily recognized.

Figure 7A:
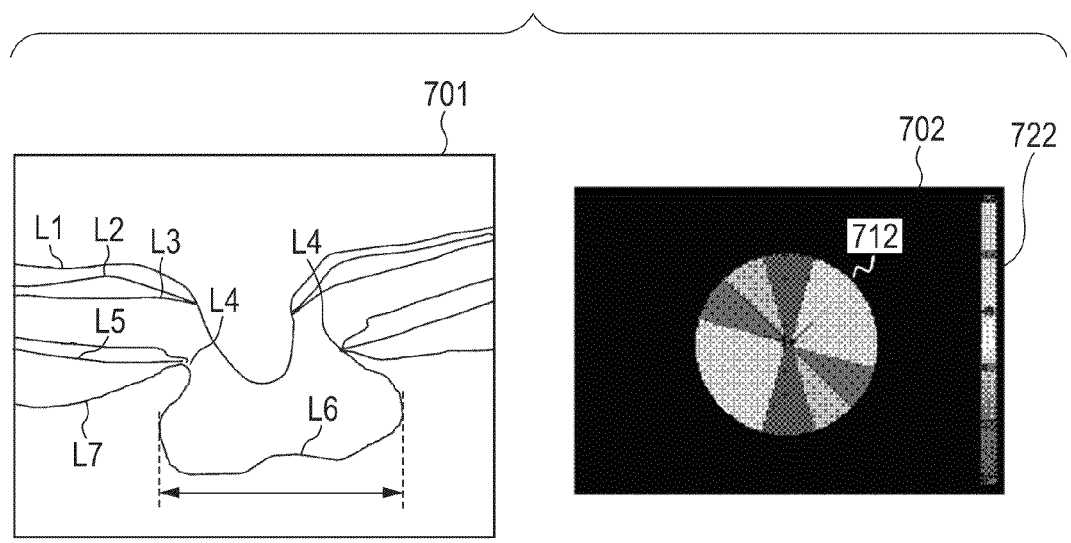
FIGS. 7A and 7B are diagrams illustrating an example of the display of the image processing apparatus.

FIG. 7A illustrates an example in the case where a tomographic image 701 and a Bowing Angle map 702 are displayed on the tomographic image observing display screen 600. In the diagram, there are shown: the tomographic image 701; an image obtained by superimposing and displaying the segmentation results (L1 to L7) showing the detection results of the respective layers of the retinal layer onto the tomographic image; and a Bowing Angle map in which the analysis results of the shape of the lamina cribrosa are shown as a 2-dimensional map. In the Bowing Angle map 702, a display range of a color map 712 of the Bowing Angle value corresponds to an area 614 (range defined by two broken lines and a double-headed arrow) of the lamina cribrosa in the tomographic image 701. A color or grey-scale chart 722 is also shown.

Figure 7B:
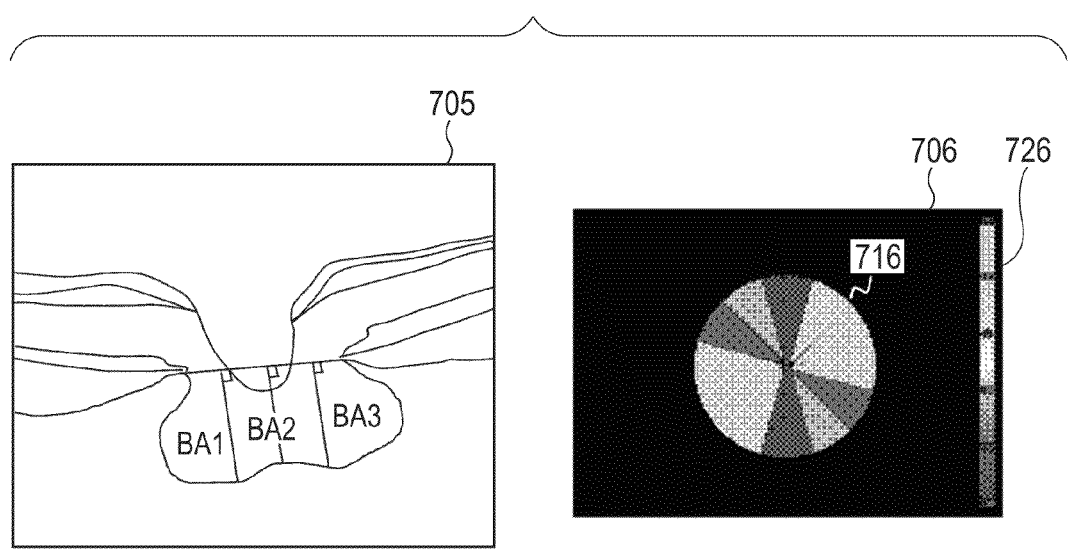

FIG. 7B illustrates a case where when a tomographic image 705 and a Bowing Angle map 706 are displayed on the tomographic image observing display screen 600, positions (BA1 to BA3) used when Bowing Angle has been analyzed are superimposed onto, and displayed on, the tomographic image. Thus, in each tomographic image, the measured positions can be visually confirmed. The color or grey-scale map 716 is displayed alongside a color or grey-scale legend 726. It is also possible to construct the display in such a manner that the operator can manually correct the measuring positions (BA1 to BA3) by using an operating unit (not shown). In the case of manually correcting the measuring positions, it is desirable that the display control unit 115 controls in such a manner that the value of Bowing Angle is displayed onto the tomographic image observing display screen 600 and the measuring positions are manually corrected and, at the same time, such a value is updated. The kinds of maps illustrated in FIGS. 6A and 6B and FIGS. 7A and 7B can be switched by selecting the first display switching unit 650. For example, a Combo Box or the like is used for the first display switching unit 650. Further, in the fundus image display unit 630, by selecting the second display switching unit 660, the superimposing displays of the 2-dimensional image and the analysis result such as fundus photograph, SLO, fluorescent fundus image, superimposing display of (fundus photograph+SLO), superimposing display of (fundus photograph+map), and the like can be switched and displayed.

In the curvatures and Bowing Angle illustrated in FIGS. 6A and 6B and FIGS. 7A and 7B, when the tomographic image and the map are displayed, as a tomographic image which is displayed, a tomographic image showing the maximum displacement (i.e. a deepest point in the lamina cribrosa) in each analysis result is displayed in an initial state. That is, it is desirable that among a plurality of tomographic images obtained by performing the radial scan around an optic nerve nipple as a center, the tomographic image of a large curvature and the tomographic image in which Bowing Angle has a minus value are selectively displayed. As for the shape of lamina cribrosa, a displacement is liable to occur in the direction of a y axis in FIG. 4B of the optic nerve nipple in the fundus image (FIG. 4B). Therefore, it is desirable that in the initial state, the tomographic image at a slice position (R1 in FIG. 4A) in the case of scanning the y-axis direction and the map are displayed side by side. Thus, the user can efficiently confirm the lamina cribrosa which is supposed to have been relatively deformed. At this time, a display form showing the position of the selected tomographic image may be displayed onto the fundus image or a 2-dimensional display form (for example, map of curvature) showing the shape of lamina cribrosa among the plurality of tomographic images. For instance, a straight line 632 (FIG. 6A) showing the scanning position is superimposed and displayed onto the map so that the position of the displayed tomographic image can be known. It is also possible to construct in such a manner that on the fundus image or 2-dimensional display form, the user can select a tomographic image that he wants to confirm a display or an analysis result from the plurality of tomographic images. For example, when the user wants to change the slice of the displayed tomographic image, by using the operating unit (not shown), e.g. by a mouse cursor 642 (FIG. 6A), the operator instructs the position of the map corresponding to the tomographic image which he wants to display. At this time, for example, if the position of the tomographic image was selected on the fundus image, the tomographic image corresponding to such a position is displayed and the corresponding position on the 2-dimensional display form is selected in an interlocking relational manner. Consequently, use efficiency of the user is improved.

As another displaying method, display colors of the measuring positions (BA1 to BA3) may be displayed in correspondence to the colors of a color bar 726 of the Bowing Angle value. For example, in the case of a negative value, the measuring position is displayed in red, and in the case of a positive value, it is displayed in blue. Further, the colored area may be superimposed and displayed onto the tomographic image so that the lamina cribrosa area used in the analysis can be known. In the case of superimposing and displaying the lamina cribrosa area, it is desirable that a degree of transparency α of the color can be set within a range of 0 to 1. For example, it is set to α=0.5.

Although not shown, the display control unit 115 allows a result (a curvature value, a Bowing Angle value, a Bowing Angle ratio, a size ratio between the lamina cribrosa area and the BMO, an area, a volume, and a thickness of the lamina cribrosa, and the like) of analysis performed by the analyzing unit 132 to be displayed as numerical values onto the tomographic image observing display screen 600. Besides the method of displaying them using the map, by showing the analysis result by the numerical values, detailed information can be presented.

<Step S207: Presence or Absence of Input of End of Image Process>

In step S207, an instruction obtaining unit (not shown) obtains an external instruction about whether or not the process of the tomographic image by the image processing apparatus 110 is finished. This instruction is input by the operator by using the operating unit (not shown). If the instruction to finish the process was obtained, the image processing apparatus 110 finishes the process. On the other hand, if the process is not finished and the analyzing process of the lamina cribrosa is switched (for example, the process is switched from the curvature analysis to the Bowing Angle analysis), the processing routine is returned to step S204 and a processing result is displayed.

In this manner, the process of the image processing apparatus 110 is executed.

According to the construction mentioned above, the shape of the lamina cribrosa is analyzed and its analysis result is displayed in a form of the map. By analyzing the shape of the lamina cribrosa and presenting the analysis result at a high visibility, an index which is effective to diagnose glaucoma early is presented.

Embodiment 2

Analysis Result of Shape of Lamina Cribrosa is Displayed by Graph

In the embodiment 1, an example in the case of displaying the analysis result of the shape of the lamina cribrosa by the form of map has been described. In the embodiment 2, an example in the case of displaying the analysis result by a form of graph will be described.

A construction of an image processing apparatus according to the embodiment 2 is similar to that of the embodiment 1 illustrated in FIG. 1 and only the function of the analysis result forming unit 133 differs from that of the embodiment 1. Therefore, a description about portions having the functions similar to those in the embodiment 1 is omitted here.

The analysis result forming unit 133 forms a graph from the analysis result of the analyzing unit 132. A processing procedure of the image processing apparatus 110 will be described hereinbelow with reference to FIGS. 2, 9A, and 9B. Since processes other than steps S205 and S206 are similar to those in the embodiment 1, their description is omitted.

<Step S205: Creation of Display Form Showing Analysis Result>

In step S205, the analysis result forming unit 133 forms various kinds of graphs from the analysis result of the lamina cribrosa obtained in step S204. In the embodiment, an example in the case of forming a curvature graph of the lamina cribrosa and a Bowing Angle graph will be described. In each tomographic image, the analysis result forming unit 133 forms the graphs by using the value corresponding to the position of the tomographic image.

Figure 9A:
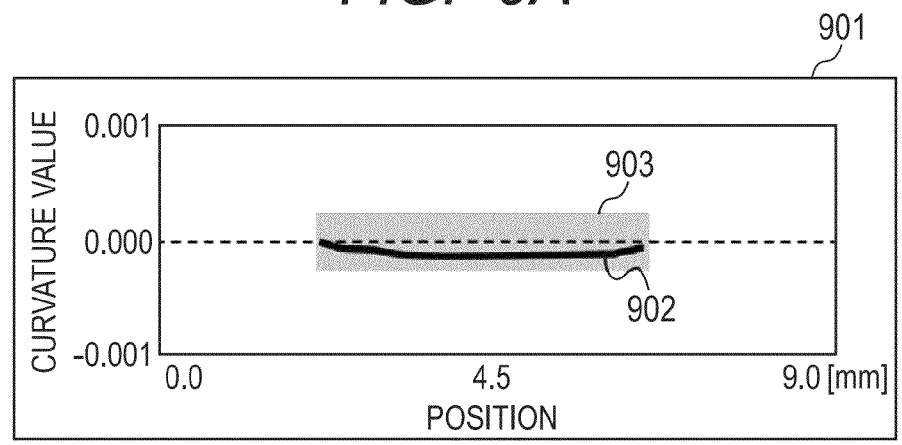
FIGS. 9A and 9B are diagrams for describing an example of presentation of an analysis result.

First, a case of forming the curvature graph will be described with reference to FIG. 9A. The curvature graph is formed for each tomographic image among a plurality of tomographic images. In the diagram, a whole curvature graph 901, a line 902 obtained by plotting curvature values in one tomographic image onto a graph, and a range 903 of values in the standard database stored in the storing unit 112 are illustrated. The range 903 corresponds to the scanning position of the tomographic image. By this graph, a degree of curve of the shape of the lamina cribrosa in each tomographic image can be grasped. Of course, the graph displayed can be a graph representing the tomographic image with the values with the greatest difference from the standard, or it can be a graph representing an average of several tomographic images, for instance.

Figure 9B:
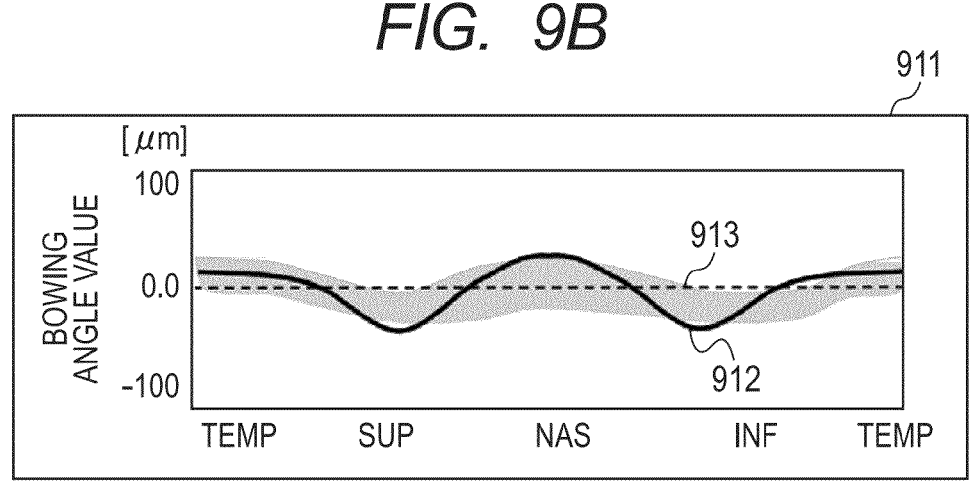

Forming the Bowing Angle graph will be described with reference to FIG. 9B. As for the Bowing Angle graph, in the case of a group of tomographic images photographed by the radial scans, a result of the whole volume is displayed to one graph. In FIG. 9B, a whole Bowing Angle graph 911, a line 912 obtained by plotting Bowing Angle values onto a graph, and a range 913 of values in the standard database stored in the storing unit 112 are illustrated. By this graph, a change in shape of the lamina cribrosa of the whole volume can be grasped.

<Step S206: Display of Display Form Showing Analysis Result>

Figure 10:
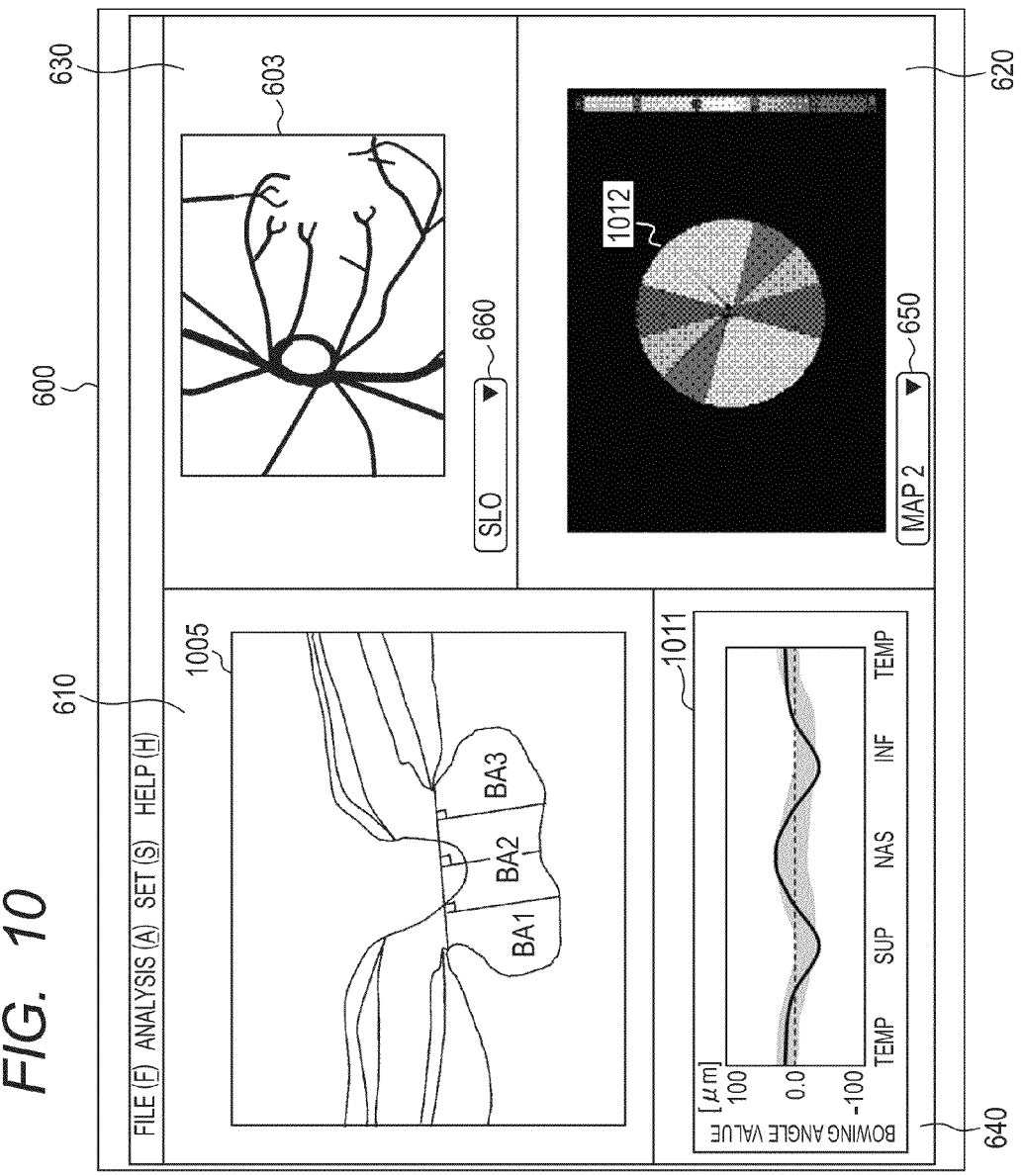
FIG. 10 is a diagram illustrating an example of the display of the image processing apparatus.

In step S206, the display control unit 115 allows the tomographic image, a detection result of the layer detected in the image processing unit 131, and various kinds of analysis results (graphs, numerical values) formed in the analysis result forming unit 133 to be displayed on the display unit 300. Such a process will now be described with reference to FIG. 10. FIG. 10 illustrates an example of a display screen which is displayed to the display unit 300 in this using form. When a tomographic image 1005, a Bowing Angle graph 1011, and a Bowing Angle map 1012 are displayed side by side on the tomographic image observing display screen 600, the positions (BA1 to BA3) used when the Bowing Angle was analyzed are superimposed and displayed on the tomographic image. It is also possible to construct the system in such a manner that when the analysis results are displayed, for example, the display colors of the measuring positions (BA1 to BA3) are changed in accordance with a discrimination result of a judgment of whether or not the value of the Bowing Angle lies within the range of the values in the standard database. For example, it is also possible to construct the system in such a manner that in the slice of the values in the standard database, they are displayed in blue, and in the slice of the values out of the standard database, they are displayed in red, or the like. The kinds of graphs that are displayed in the second analysis result display unit 640 may be switched in a coordinated manner with the timing of the kinds of maps being switched by the first display switching unit 650.

According to the construction mentioned above, the shape of the lamina cribrosa is analyzed and its analysis result is displayed in the form of graph. By analyzing the shape of the lamina cribrosa and presenting the analysis result at a high visibility, an index which is effective to diagnose glaucoma early is presented.

Other Embodiments

In each of the foregoing embodiments, the invention is realized as an image processing apparatus. However, the invention is not limited only to the image processing apparatus. The invention can be also realized as software which operates on a computer. A CPU of the image processing apparatus controls the whole computer by using a computer program or data stored in a RAM or a ROM. The function of each unit is realized by controlling the execution of software corresponding to each unit of the image processing apparatus. The computer program can be supplied to a system or apparatus through a network or various kinds of storage media.

While the present invention has been described with reference to exemplary embodiments, it is to be understood that the invention is not limited to the disclosed exemplary embodiments. The scope of the following claims is to be accorded the broadest interpretation so as to encompass all conceivable modifications and equivalent structures and functions.

This application claims the benefit of Japanese Patent Application No. 2012-015248, filed Jan. 27, 2012, which is hereby incorporated by reference herein in its entirety.

What is claimed is:

1. An image processing apparatus comprising:
an image obtaining unit configured to obtain a three-dimensional tomographic image of an eye in a depth direction;
a detection unit configured to detect a lamina cribrosa from the three-dimensional tomographic image;
an analyzing unit configured to obtain, by analyzing a shape of the detected lamina cribrosa, an analysis parameter value which includes at least one of a curvature value and a value obtained by using a Bruch membrane opening of the detected lamina cribrosa;
a generating unit configured to generate a two-dimensional map showing the obtained analysis parameter value; and
a display control unit configured to control a display unit to display the generated two-dimensional map.

2. The image processing apparatus according to claim 1, wherein the display control unit is configured to control the display unit to display the three-dimensional tomographic image and the generated two-dimensional map side by side, and to display a corresponding position of the tomographic image on the generated two-dimensional map.

3. The image processing apparatus according to claim 1, wherein the image obtaining unit is configured to obtain a plurality of three-dimensional tomographic images of the eye, the detection unit is configured to detect the lamina cribrosa from each of the plurality of three-dimensional tomographic images, and the display control unit is configured to control the display unit to display the generated two-dimensional map showing the shape of the detected lamina cribrosa, and to display a position corresponding to at least one of the plurality of three-dimensional tomographic images such that the position is superimposed onto the generated two-dimensional map.

4. The image processing apparatus according to claim 1, wherein the display control unit is configured to control the display unit to display a display form showing a detection result of the detection unit such that the display form is superimposed onto the three-dimensional tomographic image.

5. The image processing apparatus according to claim 4, wherein the detection unit is configured to detect a plurality of edge portions from a predetermined layer (BMO) of the eye shown in the three-dimensional tomographic image, and the display control unit is configured to control the display unit to display a line connecting the plurality of edge portions such that the line is superimposed onto the three-dimensional tomographic image as a display form showing the detection result.

6. The image processing apparatus according to claim 5, wherein the display control unit is configured to control the display unit to display a display form showing an area surrounded by the line and a contour of the lamina cribrosa such that the display form is superimposed onto the three-dimensional tomographic image.

7. The image processing apparatus according to claim 1, wherein the display control unit is configured to control the display unit to selectively display at least one of a plurality of three-dimensional tomographic images of the eye to be displayed, a selection being made on the basis of the shape of the lamina cribrosa shown in the respective three-dimensional tomographic image or a position of the eye where the three-dimensional tomographic image is obtained.

8. The image processing apparatus according to claim 1, wherein the display control unit is configured to control the display unit to display a fundus image of the eye, the three-dimensional tomographic image, and the generated two-dimensional map side by side, and to display the position of the tomographic image in the fundus image and the generated two-dimensional map, and wherein, in accordance with a change in the position in one of the fundus image and the generated two-dimensional map, the display of the position of the three-dimensional tomographic image in the other of the fundus image and the generated two-dimensional map is changed accordingly.

9. The image processing apparatus according to claim 1, wherein the detection unit is configured to detect the lamina cribrosa on the basis of at least one of a curvature, a thickness, an area, and a volume of the lamina cribrosa, a distance between the lamina cribrosa and another point of the three-dimensional tomographic image, and a size ratio between an area of the lamina cribrosa and another area of the three-dimensional tomographic image.

10. The image processing apparatus according to claim 1, further comprising an image processing unit configured to generate the generated two-dimensional map based on the detection result of the detection unit.

11. The image processing apparatus according to claim 10, wherein the image processing unit is configured to generate a two-dimensional map of at least one layer in the eye based on a plurality of radial tomographic images taken substantially perpendicularly to the at least one layer.

12. The image processing apparatus according to claim 10, wherein the image processing unit is configured to generate a graph comparing positional information of at least one layer in the eye with positional information of an equivalent layer in a standard eye.

13. The apparatus according to claim 1, further comprising an analysis unit configured to analyze the shape of the lamina cribrosa and generate a display form showing the shape of the lamina cribrosa.

14. The image processing apparatus according to claim 1, wherein the display control unit controls the display unit to display the generated two-dimensional map superimposed on a fundus image of the eye.

15. The image processing apparatus according to claim 1, wherein the generating unit is configured to generate a graph showing the obtained analysis parameter value, and
wherein the display control unit controls the display unit to display the generated two-dimensional map and the generated graph side by side.

16. The image processing apparatus according to claim 1, wherein the generating unit generates, as the two-dimensional map, a first two-dimensional map showing the curvature value and a second two-dimensional map showing the value obtained by using the Bruch membrane opening, and
wherein the display control unit controls the display unit to display, as the generated two-dimensional map, one of the first two-dimensional map and the second two-dimensional map by switching between the first two-dimensional map and the second two-dimensional map.

17. The image processing apparatus according to claim 1, wherein the generating unit is configured to generate a graph showing the obtained analysis parameter value,
wherein the display control unit controls the display unit to display the generated two-dimensional map and the generated graph side by side,
wherein the generating unit generates, as the two-dimensional map, a first two-dimensional map showing the curvature value and a second two-dimensional map showing the value obtained by using the Bruch membrane opening, wherein the display control unit controls the display unit to display, as the generated two-dimensional map, one of the first two-dimensional map and the second two-dimensional map by switching between the first two-dimensional map and the second two-dimensional map, wherein the generating unit generates, as the generated graph, a first graph showing the curvature value and a second graph showing the value obtained by using the Bruch membrane opening, and wherein the display control unit controls the display unit to display, as the generated graph, one of the first graph and the second graph by switching, according to the switching between the first two-dimensional map and the second two-dimensional map, between the first graph and the second graph.

18. An image processing method comprising:
obtaining a three-dimensional tomographic image of an eye;
detecting a lamina cribrosa from the three-dimensional tomographic image;
obtaining, by analyzing a shape of the detected lamina cribrosa, an analysis parameter value which includes at least one of a curvature value and a value obtained by using a Bruch membrane opening of the detected lamina cribrosa;
generating a two-dimensional map showing the obtained analysis parameter value; and
controlling a display unit to display the generated two-dimensional map.

19. The image processing method according to claim 18, further comprising:
displaying the three-dimensional tomographic image and the generated two-dimensional map side by side, and displaying a corresponding position of the three-dimensional tomographic image in the generated two-dimensional map.

20. The image processing method according to claim 18, further comprising:
obtaining a plurality of three-dimensional tomographic images of the eye;
detecting the lamina cribrosa from each of the plurality of three-dimensional tomographic images; and
displaying a two-dimensional map showing the shape of the detected lamina cribrosa, and displaying the position corresponding to at least one of the plurality of three-dimensional tomographic images such that the position is superimposed onto the two-dimensional map.

21. The image processing method according to claim 18, further comprising:
detecting a plurality of edge portions from a predetermined layer of the three-dimensional tomographic image; and
displaying a line connecting the plurality of edge portions such that the line is superimposed onto the three-dimensional tomographic image as a display form showing the detection result.

22. A non-transitory computer-readable storage medium storing a computer program which, when run on a computer, causes the computer to execute the method according to claim 18.

23. The method according to claim 18, further comprising the step of analyzing the shape of the lamina cribrosa and generating a display form showing the shape of the lamina cribrosa.

24. The image processing method according to claim 18, wherein the display unit is controlled to display the generated two-dimensional map superimposed on a fundus image of the eye.

25. The image processing method according to claim 18, further comprising:
generating a graph showing the obtained analysis parameter value,
wherein the display unit is controlled to display the generated two-dimensional map and the generated graph side by side.

26. The image processing method according to claim 18, wherein a first two-dimensional map showing the curvature value and a second two-dimensional map showing the value obtained by using the Bruch membrane opening are generated as the two-dimensional map, and
wherein the display unit is controlled to display, as the generated two-dimensional map, one of the first two-dimensional map and the second two-dimensional map by switching between the first two-dimensional map and the second two-dimensional map.

27. The image processing method according to claim 18, further comprising:
generating a graph showing the obtained analysis parameter value,
wherein the display unit is controlled to display the generated two-dimensional map and the generated graph side by side,
wherein a first two-dimensional map showing the curvature value and a second two-dimensional map showing the value obtained by using the Bruch membrane opening are generated as the two-dimensional map,
wherein the display unit is controlled to display, as the generated two-dimensional map, one of the first two-dimensional map and the second two-dimensional map by switching between the first two-dimensional map and the second two-dimensional map,
wherein a first graph showing the curvature value and a second graph showing the value obtained by using the Bruch membrane opening is generated as the generated graph, and
wherein the display unit is controlled to display, as the generated graph, one of the first graph and the second graph by switching, according to the switching between the first two-dimensional map and the second two-dimensional map, between the first graph and the second graph.

28. An image processing system comprising a photographing apparatus for obtaining a three-dimensional tomographic image of an eye and an image processing apparatus, wherein the image processing apparatus comprises:
a detection unit configured to detect a lamina cribrosa from the three-dimensional tomographic image;
an analyzing unit configured to obtain, by analyzing a shape of the detected lamina cribrosa, an analysis parameter value which includes at least one of a curvature value and a value obtained by using a Bruch membrane opening of the detected lamina cribrosa;
a generating unit configured to generate a two-dimensional map showing the obtained analysis parameter value; and
a display control unit configured to control a display unit to display the generated two-dimensional map.

29. The system according to claim 28, wherein the image processing apparatus further comprises an analysis unit configured to analyze the shape of the lamina cribrosa and generate a display form showing the shape of the lamina cribrosa.

30. An image processing apparatus comprising:
- an image obtaining unit configured to obtain a three-dimensional tomographic image of an eye in a depth direction;
- a detection unit configured to detect a lamina cribrosa from the three-dimensional tomographic image;
- an analyzing unit configured to obtain, by analyzing a shape of the detected lamina cribrosa, an analysis parameter value which includes at least one of a curvature value and a value obtained by using a Bruch membrane opening of the detected lamina cribrosa; and
- a generating unit configured to generate a two-dimensional map showing the obtained analysis parameter value.

31. An image processing method comprising:
- obtaining a three-dimensional tomographic image of an eye;
- detecting a lamina cribrosa from the three-dimensional tomographic image;
- obtaining, by analyzing a shape of the detected lamina cribrosa, an analysis parameter value which includes at least one of a curvature value and a value obtained by using a Bruch membrane opening of the detected lamina cribrosa; and
- generating a two-dimensional map showing the obtained analysis parameter value.

32. A non-transitory computer-readable storage medium storing a computer program which, when run on a computer, causes the computer to execute the method according to claim 31.

* * * * *